(12) United States Patent
Nakano et al.

(10) Patent No.: US 9,408,812 B2
(45) Date of Patent: Aug. 9, 2016

(54) COENZYME Q10-CONTAINING COMPOSITION FOR ORAL INGESTION

(71) Applicant: MITSUBISHI GAS CHEMICAL COMPANY, INC., Tokyo (JP)

(72) Inventors: Rieko Nakano, Niigata (JP); Midori Kikuchi, Niigata (JP); Kentarou Takano, Niigata (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 0 days.

(21) Appl. No.: 14/484,800

(22) Filed: Sep. 12, 2014

(65) Prior Publication Data

US 2014/0377242 A1 Dec. 25, 2014

Related U.S. Application Data

(62) Division of application No. 13/203,129, filed as application No. PCT/JP2010/053059 on Feb. 26, 2010, now abandoned.

(30) Foreign Application Priority Data

Feb. 27, 2009 (JP) ................. 2009-046291
Oct. 27, 2009 (JP) ................. 2009-246909

(51) Int. Cl.
| | | |
|---|---|---|
| *A61K 31/122* | (2006.01) | |
| *A23L 1/30* | (2006.01) | |
| *A61K 36/48* | (2006.01) | |

(Continued)

(52) U.S. Cl.
CPC ............... *A61K 31/122* (2013.01); *A23L 1/30* (2013.01); *A61K 36/48* (2013.01); *A61K 47/42* (2013.01); *A61K 47/46* (2013.01); *A23V 2002/00* (2013.01)

(58) Field of Classification Search
CPC ............................. A61K 31/122; A61K 36/00
See application file for complete search history.

(56) References Cited

U.S. PATENT DOCUMENTS

| | | | |
|---|---|---|---|
| 6,149,939 | A | 11/2000 | Strumor et al. |
| 2003/0108624 | A1 | 6/2003 | Kosbab |
| 2004/0170709 | A1 | 9/2004 | Hastings et al. |

(Continued)

FOREIGN PATENT DOCUMENTS

| | | |
|---|---|---|
| DE | 10 2005 063 062 | 7/2007 |
| EP | 1 666 445 | 6/2006 |

(Continued)

OTHER PUBLICATIONS

International Search Report Issued Mar. 30, 2010 in PCT/JP10/053059 filed Feb. 26, 2010.

(Continued)

*Primary Examiner* — Rosanne Kosson
(74) *Attorney, Agent, or Firm* — Oblon, McClelland, Maier & Neustadt, L.L.P.

(57) ABSTRACT

Disclosed are: a coenzyme Q10 composition for oral ingestion which improves the bioabsorbability of coenzyme Q10 and enables efficient ingestion of coenzyme Q10 and which is highly safe, and a pharmaceutical preparation and a functional food containing the composition for oral ingestion. Combining coenzyme Q10 and a seed processed product has made it possible to provide a coenzyme Q10-containing composition for oral ingestion excellent in bioabsorbability, and a pharmaceutical preparation and a functional food containing the composition for oral ingestion.

13 Claims, 1 Drawing Sheet

(51) Int. Cl.
*A61K 47/42* (2006.01)
*A61K 47/46* (2006.01)

(56) References Cited

U.S. PATENT DOCUMENTS

| | | |
|---|---|---|
| 2007/0253941 A1 | 11/2007 | Naidu et al. |
| 2007/0269583 A1 | 11/2007 | McMindes et al. |
| 2008/0305212 A1* | 12/2008 | Wong ............... A23C 9/1526 426/72 |
| 2010/0061969 A1* | 3/2010 | Otsubo ............... A21D 2/14 424/94.1 |

FOREIGN PATENT DOCUMENTS

| | | |
|---|---|---|
| JP | 08/214787 | 8/1996 |
| JP | 2003 169630 | 6/2003 |
| JP | 2003 321352 | 11/2003 |
| JP | 2004 026734 | 1/2004 |
| JP | 2005 002035 | 1/2005 |
| WO | 01/62226 | 8/2001 |
| WO | 02/24002 | 3/2002 |
| WO | 2008/131008 | 10/2008 |

OTHER PUBLICATIONS

Office Action issued Feb. 29, 2012 in New Zealand Application No. 594856.
Chinese Office Action Issued Jul. 23, 2012 in Patent Application No. 201080009409.X.
Guan Haijun, et al., "Extracting soybean protein concentrate continuously by ethanol and prectise of outgrowth comprehensive utilization", Soybean Bulletin, No. 6, Dec. 31, 2007, pp. 40-42 (with English abstract).
Extended European Search Report issued Aug. 3, 2012 in Patent Application No. 10746312.7.
D. Nilufer, et al., "Functionality of Soymilk Powder and Its Components in Fresh Soy Bread", Journal of Food Science, XP 55031528A, vol. 73, No. 4, May 1, 2008, pp. C275-C281.

\* cited by examiner

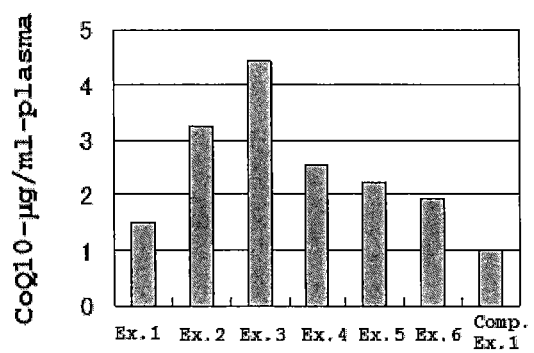

COENZYME Q10-CONTAINING COMPOSITION FOR ORAL INGESTION

TECHNICAL FIELD

The present invention relates to a composition for oral ingestion which contains a coenzyme Q10 (hereinafter referred to as CoQ10) and a seed processed product and which is excellent in bioabsorbability of CoQ10, and to a pharmaceutical preparation and a functional food containing the composition for oral ingestion.

BACKGROUND ART

CoQ10 is otherwise known as a coenzyme Q10, vitamin Q or ubiquinone, and its melting point is about 48° C. and it dissolves little in water. CoQ10 is a substance indispensable as a coenzyme when mitochondria in cells produce a high-energy phosphate compound ATP via the electron transport system thereof. CoQ10 also exists in other membrane systems than mitochondria, such as cell membrane, Golgi body, lysosome, etc., and is a vitamin-like substance that plays an important role as an antioxidant substance of scavenging peroxides that form in living bodies. CoQ10 is widely used in the field of medicines, health foods and cosmetics, as a medical remedy for congestive heart failure and as an antiaging substance based on the antioxidant effect of CoQ10.

CoQ10 is synthesized also in living bodies, and in foods, it may be contained in an amount of a few μg or so per gram of dry product of meats and eggs. However, the amount of CoQ10 to be synthesized in living bodies decreases with aging and tends to be low, and there are only an extremely few types of natural food materials having a high CoQ10 content. Accordingly, in daily meals, it is difficult to secure CoQ10 in an amount capable of compensating for the shortage thereof. CoQ10 is a fat-soluble substance and is poor in absorbability; however, in view of the safety on the administration route and the availability thereof, it is generally ingested orally.

Accordingly, it is desired to provide a simple, effective and economical technique of improving the absorbability of CoQ10 in oral administration.

For improving the absorbability of CoQ10, for example, there have been proposed a method of heating and dissolving CoQ10 in oil (for example, see Patent Reference 1), a method of using a technique of solubilization in water (for example, see Patent Reference 2), a method of using a technique of clathration with cyclodextrin (for example, see Patent Reference 3), etc.

However, the CoQ10-containing material obtained by heating and dissolving CoQ10 in oil, as described in Patent Reference 1, is problematic in that the systemic absorption in oral administration is not sufficient. The technique of solubilizing CoQ10 in water, as described in Patent Reference 2, necessarily requires a process of mixing and stirring casein Na, dextrin and CoQ10, and then freeze-drying the mixture. Another problem is that a sufficient effect could not be attained when casein Na and dextrin are not added in a large amount of at least 25 times that of CoQ10. On the other hand, the technique of clathrating CoQ10 with cyclodextrin, as described in Patent Reference 3, necessarily requires a complicated step for clathration, and is therefore problematic in that the production cost increases.

CITATION LIST

Patent References

Patent Reference 1: Japanese Patent 3549019
Patent Reference 2: JP-A 2003-169630
Patent Reference 3: JP-T 2003-520827

SUMMARY OF THE INVENTION

Problems that the Invention is to Solve

An object of the present invention is to provide a CoQ10-containing composition for oral ingestion which is easy to produce and is excellent in economical potential and excellent in systemic absorption, as well as a pharmaceutical preparation and a functional food containing the composition for oral ingestion.

Means for Solving the Problems

The present invention relates to a composition for oral ingestion in which the bioabsorbability of CoQ10 is extremely increased according to a simple and economical method of adding and mixing a seed processed product mentioned below, and to a pharmaceutical preparation and a functional food containing the composition for oral ingestion.

Specifically, the present invention provides the following (1) to (18):

(1) A composition for oral ingestion containing a seed processed product and a coenzyme Q10.

(2) The composition for oral ingestion of the above (1), wherein the seed processed product is at least one selected from a soy protein or a soy protein hydrolyzate.

(3) The composition for oral ingestion of the above (2), wherein the soy protein is an acid processed product, an alkali processed product or an alcohol processed product.

(4) The composition for oral ingestion of the above (2), wherein the soy protein hydrolyzate is an enzyme hydrolyzate.

(5) The composition for oral ingestion of the above (1), wherein the seed processed product is one or more powders selected from a seed ground powder and a powder obtained from a seed extract.

(6) The composition for oral ingestion of the above (5), wherein the seed ground powder is a powder obtained by grinding one or more parts selected from the seed coat, the albumen and the germ of seeds.

(7) The composition for oral ingestion of the above (6), wherein the seed coat, the albumen and the germ of seeds are the seed coat, the albumen and the germ of roasted seeds, or the seed coat, the albumen and the germ of defatted seeds.

(8) The composition for oral ingestion of the above (5), wherein the powder obtained from a seed extract is a powder obtained by drying an extract that has been extracted from one or more parts selected from the seed coat, the albumen and the germ of seeds, by squeezing or by the use of water or an alcohol-containing aqueous solvent.

(9) The composition for oral ingestion of the above (8), wherein the seed coat, the albumen and the germ of seeds are the seed coat, the albumen and the germ of heat-treated seeds, or the seed coat, the albumen and the germ of defatted seeds.

(10) The composition for oral ingestion of the above (8) or (9), wherein the powder obtained from a seed extract is a powder prepared by drying the protein fraction of the extract that has been extracted from one or more parts selected from the seed coat, the albumen and the germ of seeds, by squeezing or by the use of water or an alcohol-containing aqueous solvent.

(11) The composition for oral ingestion of the above (5), wherein one or more powders selected from a seed ground powder and a powder obtained from a seed extract are powders obtained from seeds of a pea family (*Fabaceae*).

(12) The composition for oral ingestion of the above (11), wherein one or more powders selected from a seed ground powder and a powder obtained from a seed extract are powders obtained from soy seeds (*Glycine max*).

(13) The composition for oral ingestion of the above (12), wherein the powder obtained from soy seeds is a whole soy powder or toasted whole soy flour, or a defatted soy powder or toasted defatted soy flour.

(14) The composition for oral ingestion of the above (12), wherein the powder obtained from soy seeds is a soymilk powder, a soy protein powder or a soy protein hydrolyzate powder.

(15) The composition for oral ingestion of any of the above (1) to (14), wherein the blend ratio of the seed processed product to the coenzyme Q10 is 0.01 times by mass or more.

(16) The composition for oral ingestion of any of the above (1) to (15), wherein the coenzyme Q10 is one or more selected from oxidized and reduced coenzyme Q10.

(17) A pharmaceutical preparation containing the coenzyme Q10 composition for oral ingestion of any of the above (1) to (16).

(18) A functional food containing the coenzyme Q10 composition for oral ingestion of any of the above (1) to (16).

Advantage of the Invention

Using the composition containing both CoQ10 and a seed processed product of the present invention increases the bioabsorbability of CoQ10 simply, economically and remarkably. In addition, since the seed processed product can be ingested, it is possible to simultaneously enjoy the nutrient effect of the product.

BRIEF DESCRIPTION OF THE DRAWING

FIG. 1 Bioabsorbability test results of CoQ10 in rats.

DETAIL DESCPITION OF THE INVENTION

The present invention relates to a CoQ10 composition for oral ingestion, in which CoQ10 that is fat-soluble and poorly dispersible in water and is poor in bioabsorbability can be dispersed in water and which is excellent in bioabsorbability, and this is characterized by containing a seed processed product and a coenzyme Q10.

The present inventors have assiduously studied substances that are highly safe and can increase the bioabsorbability of CoQ10 simply and economically even when a little amount thereof is added, and as a result, have found that when a seed processed product is added thereto, the bioabsorbability of CoQ10 can be extremely increased even when the amount added is small, and have completed the present invention.

In the present invention, CoQ10 to be used may be any of an oxidized type (Chemical formula 1) or a reduced type (chemical formula 2). Its production may be in any method of organic synthesis or fermentation.

CoQ10 can be produced according to a synthetic method of using solanesol and benzoquinone, or a fermentation method of using microorganisms such as yeast, bacteria, etc.

[Chemical Formula 1]

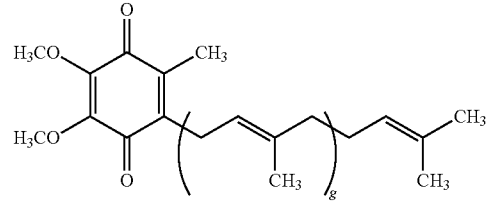

(1)

[Chemical Formula 2]

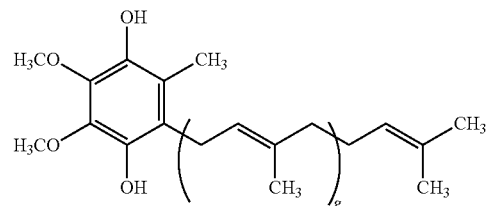

(2)

As the seed processed product for use in the present invention, preferred are at least one selected from a soy protein or a soy protein hydrolyzate, or one or more powders selected from a seed ground powder and a powder obtained from a seed extract.

The soy protein and its hydrolyzate for use in the present invention are produced from soybean, and the production methods for these are not specifically defined. An ordinary production method is described, in which defatted soybean is processed in a diluted alkali solution (with pH of from 8 to 9) for protein extraction, the insoluble ingredient is precipitated through centrifugation to collect the protein, and this is washed with water, then suspended in water and spray-dried. Also mentioned are an acid processed product that is prepared by adding, after alkali extraction, an acid to remove the soluble ingredient, or an alcohol processed product prepared by washing with alcohol after alkali extraction, as well as an enzymatically hydrolyzed product to be prepared through additional enzymatic decomposition, or an alkali processed product prepared through treatment with alkali. Naturally, undefatted soybean can also be used here as the starting material.

The soy protein for use in the present invention is not specifically defined, for which is usable a soy protein powder.

The soy protein powder includes an extracted soy protein powder, a concentrated soy protein powder, a separated soy protein powder, etc. One ordinary production process for the starting material soymilk to be the basis of these comprises the following steps. Specifically, the process comprises a husking step for starting material soybean→a step of hypocotyl removal (removal of soil bacteria, unpleasant taste ingredients)→a dipping step (swelling, removal of oligosaccharides)→a triturating step (powdering)→a heating step (85 to 95° C., inactivation of trypsin inhibitor, lipoxygenase, etc.) →a step of protein extraction and separation (removal of soy pulp)→an adjustment step (addition of vegetable oil, sugar, etc.)→a step of sterilization→a step of homogenization→a filling step. Recent improvement in production technique has made it possible to produce high-quality soymilk products with no smell of green.

On the other hand, breed improvement for soybean is being promoted, in which the ingredient to cause green smell or astringent taste peculiar to soybean is reduced; and a soy variety, Kinusayaka (Soy Norin No. 130) or the like in which lipoxygenase to cause green smell is removed and in which group A acetylsaponin to exhibit strong astringent taste is deleted has been bred, and with that, it has become possible to produce higher-quality soymilk with little green smell or astringent taste.

The protein content of a dry soymilk powder is from 40 to 44% or so, and the protein content of its partially-purified, extracted soy protein powder is 60% or so.

A concentrated soy protein is basically a substance prepared by removing saccharides and other soluble ingredients from a defatted soy powder, and mainly comprises protein, cellulose, hemicellulose and the like, in which the protein content is about 70%. The concentrated soy protein is one generally prepared by washing defatted soybean with ethyl alcohol having a concentration of from 50 to 70% to remove saccharides, ashes and other minor ingredients, and then grinding, drying and powdering it.

A separated soy protein has the highest degree of purification among soy proteins, and is obtained by processing a defatted soy powder with a diluted alkali solution (with pH of from 8 to 9) for protein extraction, collecting the protein by precipitating the insoluble ingredient through centrifugation, followed by washing with water, suspending in water and spray-drying it.

The soy protein includes an acid processed product, an alkali processed product, an alcohol processed product, etc.; and the soy protein hydrolyzate includes an enzyme hydrolyzate, etc.

The protein content in the soy protein or its hydrolyzate for use in the invention is preferably 40% or more, more preferably 60% or more.

The present invention makes it possible to produce a composition for oral ingestion not only capable of increasing the bioabsorbability of CoQ10 but also simultaneously capable of taking advantage of excellent nutritional characteristics thereof.

The soy protein and its hydrolyzate usable in the present invention are available on the market, and such commercial products are usable here. For example, there are mentioned Fuji Oil's SOYASOUR, HI-NUTE Series, FUJIPRO Series, SUNLOVER Series, PROLEENA Series; Nisshin Oillio's NEWSOYME, NEWCOMITEX, PROCON, SORPI, SOYA-FLOUR, ALFAPLUS, etc.

In the present invention, when CoQ10 and a soy protein or its hydrolyzate are mixed, CoQ10 and a soy protein or its hydrolyzate may be mixed in powder to prepare the composition.

A soy protein or its hydrolyzate may easily form a dispersion thereof in water or alcohol, which may be used here for mixing. The blend ratio of the soy protein or its hydrolyzate to CoQ10 is preferably 0.01 times or more, more preferably 0.05 times or more.

The mixing method is not specifically defined; however, since the melting point of CoQ10 is around 50° C., preferred is a method of not giving too much heat in mixing. In preparing the composition, preferably, the mixing is at −20 to 40° C.

In that manner, according to the present invention, it has become possible to produce, from a non-bulky preparation nearly equal to a preparation comprising CoQ10, a composition capable of simultaneously and easily ingesting soybean that is specifically noted from the nutritional benefits thereof.

The size of the powder comprising CoQ10 and a soy-derived powder is, irrespective of the type thereof, preferably from 0.1 to 500 μm each, more preferably from 5 to 180 μm.

The seed powder or the powder obtained from a seed extract that is used in the present invention as a seed processed product is one prepared by powdering seeds or a seed extract.

Specific examples of the ground powder of seeds include a powder obtained by grinding one or more parts selected from the seed coat, the albumen and the germ of seeds; a powder obtained by grinding a roasted one prepared by roasting one or more parts selected from the seed coat, the albumen and the germ of seeds; a powder obtained by grinding a defatted one prepared by defatting one or more parts selected from the seed coat, the albumen and the germ of seeds, etc.

The ground powder obtained from a seed extract includes a powder obtained by drying an extract that has been extracted from one or more parts selected from the seed coat, the albumen and the germ of seeds, by squeezing or by the use of water or an alcohol-containing aqueous solvent; a powder obtained by drying an extract that has been extracted from a heat-treated product of one or more parts selected from the seed coat, the albumen and the germ of seeds; a powder prepared by drying a protein fraction of an extracted that has been extracted from one or more parts selected from the seed coat, the albumen and the germ of seeds, etc.

The seeds usable here as the object are preferably seeds that are ordinarily used as food, and, for example, there are mentioned powders obtained from the seeds of plants belonging to Malvaceae (cotton), Sterculiaceae (*cacao*), Rubiaceae (coffee), Cruciferae (rapeseed), Ginkgoaceae (*ginkgo*), Poaceae (wheat, rice, corn), Cucurbitaceae (pumpkin, watermelon), Anacardiaceae (cashew nut, pistachio), Compositae (sunflower), Juglandaceae (walnut, pecan), Pedaliaceae (sesame), Lamiaceae (*perilla*), Polygonaceae (buckwheat), Theaceae (*camellia*), Hippocastanaceae (horse chestnut), Nelumbonaceae (*lotus*), Rosaceae (apricot), Vitaceae (grape), Fagaceae (chestnut), Trapaceae (water chestnut), Pinaceae (pine), Fabaceae (soybean, adzuki bean, pea, broad bean, chickpea, common bean, peanut, etc.), Oleaceae (olive), Arecaceae (coconut), Proteaceae (*macadamia*), etc. Of the seeds of those plants, preferred are the seeds of plants of Fabaceae, Rubiaceae, Pedaliaceae and Poaceae that are widely cultivated as crop plants; and more preferred are the seeds of plants of Fabaceae. Above all, soybean cultivated especially on a major scale is the most preferred from the viewpoint of the economical benefits and the advantages thereof.

An embodiment of using soybean that belongs to Fabaceae as the plant seeds for the powder starting material to be obtained from a seed powder or a seed extract is described below.

An ordinary ground powder of soybean includes a toasted soy flour, a whole fat soy powder, a defatted soy powder, etc. As the powder obtained from soy seeds for use in the present invention, preferred are whole soy powder, toasted whole soy flour, defatted soy powder, toasted defatted soy flour.

Toasted soy flour is a food prepared by toasting and powdering soybean, in which the lipoxygenase is, by toasting thereof, heated and inactivated without being brought into contact with unsaturated fatty acids. Accordingly, one not having any unpleasant smell but having a fragrant flavor can be prepared. In addition, husking or hypocotyl removal may be attained for further removing the unpleasant smell.

Soybean roasting may be attained by heating whole soybean or defatted soybean in a flat oven at from 100 to 200° C. for 10 to 30 minutes, generally at a temperature of 150° C. for 15 minutes or so. At present, for the purpose of obtaining a toasted soy flour more excellent in appearance and taste, much employed is a high-temperature short-time roasting method with a rotary roaster using roasting sand at around 220° C. for a period of 30 seconds or so. According to this roasting treatment, physiologically-unfavorable ingredients existing in raw soybean, such as a trypsin inhibition factor or the like to cause digestion absorption inhibition, may be inactivated and removed. Toasted soy flour or raw soy powder may be produced by grinding whole soybean, but for quality improvement, a husking step may be incorporated in the process by roughly grinding soybean prior to the grinding step.

In addition, as the powder obtained from soybean, also usable is a powder obtained from a soy seed extract such as the above-mentioned soymilk powder, soy protein powder, soy protein hydrolyzate powder, etc.

The grinding and triturating method for soybean is not specifically defined, for which favorably employed is an apparatus such as a stone or ceramic-made mortar or a coffee mill. Soybean to be ground and triturated may be previously heat-treated, or may be an unheated one, or may be a matured or unmatured one. Dry soybean may be used directly as it is, or may be used after dipped in water or in hot water for a predetermined period of time. The thus-obtained, ground and triturated product may be, if desired, classified through sieving to remove those having a large grain size, and may be again ground and triturated thereby giving a ground and triturated product that is finer and has better quality, at high yield. The obtained triturated product may be filtered through a suitable filtering material such as a bleached cloth to give a liquid juice (soymilk).

The thus-obtained, ground and triturated product is dried for preventing degradation through decomposition, etc. The drying method is not specifically defined, for which, for example, the product is dried with a rack-type aeration drier, an aeration heating drier, a freezing drier, a drum drier, a spray drier, etc. The drying temperature and the drying time may be suitably determined in consideration of the taste and the preservability of the dried powder.

Regarding the variety of soybean to be used here, there are many types of soybean such as Fukuyutaka (Soy Norin No. 73), Enrei (Soy Norin No. 57), Suzuyutaka (Soy Norin No. 76), Tamahomare (Soy Norin No. 72), Tachinagaha (Soy Norin No. 85), Sachiyutaka (Soy Norin No. 116), Yukihomare (Soy Norin No. 118) and others with no specific limitation thereon; however, the variety thereof to be used may be selected in consideration of the difficulty level in husking; the appearance characteristics such as color, grain form, grain size, etc.; the ingredient characteristics such as protein content, fat content, whole sugar content, dissolved solid content, ash content, seed coat ratio, water absorption, etc.; and the processability characteristics such as fracture strength, solid content extraction ratio, soymilk protein content, color and organoleptic evaluation, etc.

Recently, some varieties given additional characteristics have been created by breeding effort. There have been bred a variety where a lipoxygenase which is an enzyme to cause the green smell of soybean is completely deleted, Ichihime (Soy Norin No. 103), L-Star (Soy Norin No. 115), Suzusayaka (Soy Norin No. 125), etc.; and a variety where the α-subunit of soy allergen protein is deleted, Yumeminori (Soy Norin No. 117), etc. In addition, a variety where the content of isoflavon, which is specifically noted as a functional ingredient, is high, Fukuibuki (Soy Norin No. 122) has also been bred.

Isoflavon contained in soybean has a structure similar to that of female hormone and is considered to have a complementary effect for female hormone. In previous studies, there have been reported the functions thereof for prevention of osteoporosis, relaxation of climacteric symptoms such as hot flashes and the like, prevention of cancer, prevention of diabetes, etc. US Food and Drug Administration has specifically noted the cholesterol-lowering effect of soy protein, and has admitted the expression to the effect that the foods containing 6.25 g per serving (25 g a day) of soy protein could be foods capable of reducing the risk of cardiac diseases.

As in the above, using a powder obtained from a ground powder or extract of soybean makes it possible to produce a composition for oral ingestion not only capable of increasing the bioabsorbability of CoQ10 but also simultaneously capable of taking advantage of excellent agricultural and nutritional characteristics that various varieties of soybean have.

In the present invention, when CoQ10 is mixed with a soy powder, a predetermined amount of CoQ10 is taken and mixed with a powder prepared from a seed ground product or a seed extract.

For mixing CoQ10 and a soy powder, there may be employed a method of mixing a crystal of CoQ10 directly as it is, or CoQ10 may be previously melted or dissolved in fat, oil or the like to be liquid, and thereafter it may be added to and dusted with a toasted soy flour or a soy protein powder to thereby mix them. A mixture of a reduced CoQ10 and a soy powder may be produced, for example, by reducing an oxidized CoQ10 with a reducing agent such as sodium hydrosulfite, sodium borohydride or the like and, like that for the oxidized CoQ10, mixing it with a toasted soy flour or a soy protein powder. In this case, the system may be processed in an oxygen-free condition such as in a nitrogen current or the like, to thereby prevent the reduced Q10 from changing into the oxidized Q10.

In the present invention, the blend ratio of CoQ10 and the seed processed product is preferably 0.01 times or more by mass, more preferably 0.1 times or more as the blend ratio of the seed processed product to CoQ10. On the other hand, the uppermost limit is not specifically defined but is preferably not larger than 25 times or so, from the viewpoint of securing the predetermined amount of CoQ10 capable of being taken per the composition. In that manner, according to the present invention, it has become possible to produce, from a non-bulky preparation nearly equal to a preparation comprising CoQ10 alone, a composition capable of simultaneously and easily ingesting seeds, especially soybean that are specifically noted from the nutritional benefits thereof.

As in the above, by employing an extremely simple method of merely mixing a seed processed product and CoQ10, it has become possible to remarkably increase the bioabsorbability of CoQ10. The mechanism is presumed as follows: An adsorption adduct may be formed between the protein, especially a high-molecular protein in the seed processed product (for example, in soybean) and CoQ10, or the dispersibility of the poorly water-soluble CoQ10 in water may be enhanced since the high-molecular protein has emulsifiability, whereby the trapping absorbability of CoQ10 in small intestines could be enhanced.

The administration form of the composition for oral ingestion of CoQ10 is not specifically defined, and may be suitably selected in accordance with the use thereof. The composition for oral ingestion of the present invention can be used as foods, functional foods, medicines or quasi drugs for humans or animals. The functional foods as referred to herein mean foods to be taken for the purpose of maintenance of good health or for nutritional support in place of meals, for example, health foods, dietary supplements, foods with nutrient function claims, nutrient insurance foods, etc. General forms of the composition for oral ingestion of the present invention include capsules, tablets, chewables, pills, drinks, etc., to which, however, the present invention should not be limited.

More concretely, the composition may be added to ordinary foods, for example, miso (fermented soybean paste), soy sauce, instant miso soup, ramen, pan-fried noodles, curry, corn soup, mapo tofu (Chinese dish from the Sichuan province), mapo eggplant, pasta sauce, pudding, cake, bread, etc.

The preparation comprises the composition containing at least CoQ10 and a seed processed product, and may further contain any optional active ingredient. The preparation can be produced by mixing the ingredients along with one or more processing carriers acceptable for medicines and foods, according to any desired method known in the technical field of drug formulation.

When the composition is formed as a oral preparation, for example, usable therein are vehicle, binder, disintegrator, lubricant, dispersant, suspension agent, emulsifier, diluent, buffer, antioxidant, antibacterial, etc.

On the other hand, when the composition is produced as a functional food product, usable therein are food additives, for example, sweetener, artificial color, preservative, viscosity stabilizer, antioxidant, colorant, bleaching agent, antibacterial antifungal, gum base, bitter flavor, enzyme, gloss agent, acidic ingredient, seasoning, emulsifier, reinforcing agent, production aid, pepper, pepper extract, etc.

EXAMPLES

The present invention is described in more detail with reference to the following Examples and Comparative Examples; however, the invention is not limited to these examples.

<CoQ10 Bioabsorbability Test>
(Feeding Method)

Eight-week age SD rats (male, 3 rats in one group, body weight 250 to 300 g, kept feed-deprived from the evening of the day before the test to the end of the test) were forcedly made to orally ingest the composition for oral ingestion prepared in Examples and Comparative Examples, in an amount of 100 mg CoQ10/kg rat weight; and in 3 hours after the administration, a blood sample was collected from the tail vein of each rat, using a heparin-added vacuum blood collection tube, and the plasma was separated from it.

(Determination of CoQ10 Amount in Blood)

One ml of the collected plasma was taken, and 2.5 ml of 2% FeCl3-ethanol solution was added to and mixed with it so that all CoQ10 in the plasma could be an oxidized one, whereby the reduced CoQ10 was changed to an oxidized CoQ10. Next, 5 ml of hexane was added thereto and vigorously mixed, then the oxidized CoQ10 in the plasma was extracted out, centrifuged, and the hexane layer was collected in a different test tube. This operation was repeated three times, and 15 ml of the obtained hexane extract was concentrated under reduced pressure using an evaporator [1.3 to 13.3 kPa (10 to 100 Torr)], and subsequently, 0.2 ml of isopropanol was added thereto for dissolution. 0.2 ml of the obtained isopropanol solution was analyzed through HPLC under the condition mentioned below, and the concentration in one ml of the plasma was computed. The results are shown in Table 1 and Table 2.

HPLC Analysis Condition:
Column: YMC PACK ODS-A,
Mobile phase: methanol/hexane=4/1 (v/v),
Detection wavelength: 275 nm,
Flow rate: 1.0 ml/min,
Column temperature: 30° C.,
Reduced CoQ10 retention time: 10 min,
Oxidized CoQ10 retention time: 16 min.

Example 1

8 g of oxidized CoQ10 (by Mitsubishi Gas Chemical Company, Inc.) and 2 g of a seed processed product, soy protein prepared by extracting and separating soy oil from soybean followed by alcohol-washing the defatted soybean to remove soluble saccharides, were put into a plastic bottle, well shaken and mixed, and then dispersed in olive oil to prepare a composition for oral ingestion having a concentration of 12.5% by mass. The obtained composition for oral ingestion was tested according to the CoQ10 bioabsorbability test.

Example 2

This is the same as in Example 1, except that 8 g of oxidized CoQ10 (by Mitsubishi Gas Chemical Company, Inc.) and 2 g of a seed processed product, soy protein prepared by extracting and separating soy oil from soybean, then alcohol-washing the defatted soybean to remove soluble saccharides and processing it for enzymatic hydrolysis, were used.

Example 3

This is the same as in Example 1, except that 8 g of oxidized CoQ10 (by Mitsubishi Gas Chemical Company, Inc.) and 2 g of a seed processed product, soy protein prepared by extracting and separating soy oil from soybean, then removing the insolubles from the defatted soybean and alkali-processing the defatted soybean, were used.

Example 4

This is the same as in Example 1, except that 8 g of oxidized CoQ10 (by Mitsubishi Gas Chemical Company, Inc.) and 2 g of a seed processed product, soy powder prepared by heating and grinding husked soybean after husk removal from soybean, were used.

Example 5

This is the same as in Example 1, except that 8 g of oxidized CoQ10 (by Mitsubishi Gas Chemical Company, Inc.) and 2 g of a seed processed product, soy powder prepared by extracting and separating soy oil from soybean and then grinding the defatted soybean, were used.

Example 6

This is the same as in Example 1, except that 9.5 g of oxidized CoQ10 (by Mitsubishi Gas Chemical Company, Inc.) and 0.5 g of a seed processed product, soy protein prepared by extracting and separating soy oil from soybean, then alcohol-washing the defatted soybean to remove soluble saccharides and processing it for enzymatic hydrolysis, were used.

Comparative Example 1

This is the same as in Example 1, except that 10 g of oxidized CoQ10 was used but a seed processed product was not used.

The results (average of 2 to 5 rats) of the CoQ10 bioabsorbability test with rats of the compositions of Examples 1 to 6 and Comparative Example 1 are shown in Table 1 below and in FIG. 1.

TABLE 1

| Example | CoQ10 Used | Additive | Composition Ratio (ratio by mass) CoQ10 | Additive | Dispersant | Dose of CoQ10 mg/kg-rat | Administration Condition | Blood Collection Condition | Quantitative Value of CoQ10 μg/ml-plasma |
|---|---|---|---|---|---|---|---|---|---|
| Example 1 | oxidized Q10 | alcohol-washed soy protein | 80 | 20 | olive oil | 100 | feed-deprived | after 3 hrs | 1.50 |
| Example 2 | oxidized Q10 | enzyme-hydrolyzed soy protein | 80 | 20 | olive oil | 100 | feed-deprived | after 3 hrs | 3.24 |
| Example 3 | oxidized Q10 | alkali-processed soy protein | 80 | 20 | olive oil | 100 | feed-deprived | after 3 hrs | 4.43 |
| Example 4 | oxidized Q10 | husked soy powder | 80 | 20 | olive oil | 100 | feed-deprived | after 3 hrs | 2.54 |
| Example 5 | oxidized Q10 | defatted soy powder | 80 | 20 | olive oil | 100 | feed-deprived | after 3 hrs | 2.24 |
| Example 6 | oxidized Q10 | enzyme-hydrolyzed soy protein | 95 | 5 | olive oil | 100 | feed-deprived | after 3 hrs | 1.95 |
| Comparative Example 1 | oxidized Q10 | — | 100 | 0 | olive oil | 100 | feed-deprived | after 3 hrs | 1.02 |

Example 7

20 parts by mass of oxidized CoQ10 (by Mitsubishi Gas Chemical Company, Inc.) and 80 parts by mass of a seed processed product, soymilk powder (by Fuji Oil Co., Ltd.) were put in a mortar and well mixed, and then dispersed in water to prepare a composition for oral ingestion having a concentration of 12.5% by mass. The obtained composition for oral ingestion was tested according to the CoQ10 bioabsorbability test.

Example 8

This is the same as in Example 7, except that 20 parts by mass of oxidized CoQ10 (by Mitsubishi Gas Chemical Company, Inc.) and 80 parts by mass of a seed processed product, soymilk powder (by Fuji Oil Co., Ltd.) were put in a mortar and well mixed, and then dispersed in olive oil to prepare a composition for oral ingestion having a concentration of 12.5% by mass, and this was tested.

Example 9

This is the same as in Example 8, except that a soy powder (by Ikedaya) prepared from a lipoxygenase-deleted soybean "Suzusayaka (Soy Norin No. 125)" was used in place of the soymilk powder.

Example 10

This is the same as in Example 8, except that a mixture prepared by mixing 80 parts by mass of oxidized CoQ10 (by Mitsubishi Gas Chemical Company, Inc.) and 20 parts by mass of a soy protein powder (by Nisshin OilliO Group, Ltd.) was used.

Example 11

This is the same as in Example 8, except that a mixture prepared by mixing 80 parts by mass of oxidized CoQ10 (by Mitsubishi Gas Chemical Company, Inc.) and 20 parts by mass of a soymilk powder (by Fuji Oil Co., Ltd.) was used.

Example 12

This is the same as in Example 8, except that a mixture prepared by mixing 20 parts by mass of oxidized CoQ10 (by Mitsubishi Gas Chemical Company, Inc.) and 80 parts by mass of a sesame powder (by ShinSei Co., Ltd.) was used.

Example 13

This is the same as in Example 8, except that a mixture prepared by mixing 80 parts by mass of oxidized CoQ10 (by Mitsubishi Gas Chemical Company, Inc.) and 20 parts by mass of a sesame powder (by ShinSei Co., Ltd.) was used.

Example 14

This is the same as in Example 8, except that a mixture prepared by mixing 90 parts by mass of oxidized CoQ10 (by Mitsubishi Gas Chemical Company, Inc.) and 10 parts by mass of a soy protein hydrolyzate (HSP310 by Tatua Japan Co., Ltd.) was used.

Example 15

This is the same as in Example 8, except that a mixture prepared by mixing 95 parts by mass of oxidized CoQ10 (by Mitsubishi Gas Chemical Company, Inc.) and 5 parts by mass of a soy protein powder (by Nisshin OilliO Group, Ltd.) was used.

Example 16

This is the same as in Example 8, except that a toasted soy flour (by ShinSei Co., Ltd.) was used in place of the soymilk powder.

Example 17

This is the same as in Example 8, except that a mixture prepared by mixing 20 parts by mass of oxidized CoQ10 (by Mitsubishi Gas Chemical Company, Inc.) and 80 parts by mass of a ground product of roasted coffee bean (harvested in Columbia, manufactured by Key Coffee Inc.) was used.

Example 18

This is the same as in Example 8, except that a mixture prepared by mixing 80 parts by mass of oxidized CoQ10 (by Mitsubishi Gas Chemical Company, Inc.) and 20 parts by mass of a ground product of roasted coffee bean (harvested in Columbia, manufactured by Key Coffee Inc.) was used.

Example 19

This is the same as in Example 8, except that a mixture prepared by mixing 99 parts by mass of oxidized CoQ10 (by Mitsubishi Gas Chemical Company, Inc.) and 1 part by mass of a soy protein powder (by Nisshin OilliO Group, Ltd.) was used.

Example 20

This is the same as in Example 8, except that a mixture prepared by mixing 20 parts by mass of oxidized CoQ10 (by Mitsubishi Gas Chemical Company, Inc.) and 80 parts by mass of a wheat flour (high-gluten flower, by Nisshin flour Milling Inc.,) was used.

Example 21

This is the same as in Example 7, except that a mixture prepared by mixing 20 parts by mass of reduced CoQ10, which had been prepared from oxidized CoQ10 (by Mitsubishi Gas Chemical Company, Inc.) with a reducing agent, sodium hydrosulfite, and 80 parts by mass of a toasted soy flour (by ShinSei Co., Ltd.) was used.

Comparative Example 2

This is the same as in Example 8, except 100 parts by mass of reduced CoQ10 was used but a seed processed product was not used.

The results (average of 2 to 5 rats) of the CoQ10 bioabsorbability test with rats of the compositions of Examples 7 to 21 and Comparative Examples 1 and 2 are shown in Table 2 below.

As known from Table 1 and Table 2, the composition for oral ingestion obtained from CoQ10 and a seed processed product such as typically soybean, belonging to the present invention, comprises the above-mentioned constitution and is excellent in systemic absorption, and therefore exhibits excellent bioabsorbability.

INDUSTRIAL APPLICABILITY

The composition for oral ingestion of the present invention, which contains a seed processed product and CoQ10, is useful in the fields of medicines and functional foods such as health foods, dietary supplements, etc.

The invention claimed is:
1. A composition suitable for oral ingestion, consisting of:
   a) a product, wherein the product is selected from the group consisting of a soy protein, a soy protein hydrolyzate, a seed ground powder, a powder obtained from a seed extract, and a combination thereof;
   b) coenzyme Q10; and
   c) water or oil or water and oil, wherein the product and the coenzyme Q10 are dispersed in the water, oil, or water and oil, thereby forming a dispersion, and wherein the dispersion is made by combining only the product and the coenzyme Q10 in the water, oil, or water and oil; and by mixing the product and the coenzyme Q10 in the water, oil, or water and oil.
2. The composition of claim 1, wherein the soy protein is isolated by extracting soybeans with an alkali solution and treating the alkali extract with an acid solution or an alcohol.
3. The composition of claim 1, wherein the soy protein hydrolyzate is an enzyme hydrolyzate.

TABLE 2

| Example | CoQ10 Used | Additive | Composition Ratio (ratio by mass) CoQ10 | Additive | Dispersant | Dose of CoQ10 mg/kg-rat | Administration Condition | Blood Collection Condition | Quantitative Value of CoQ10 µg/ml-plasma |
|---|---|---|---|---|---|---|---|---|---|
| Example 7 | oxidized Q10 | soymilk powder | 20 | 80 | water | 100 | feed-deprived | after 3 hrs | 3.80 |
| Example 8 | oxidized Q10 | soymilk powder | 20 | 80 | olive oil | 100 | feed-deprived | after 3 hrs | 3.61 |
| Example 9 | oxidized Q10 | soy powder | 20 | 80 | olive oil | 100 | feed-deprived | after 3 hrs | 3.35 |
| Example 10 | oxidized Q10 | soy protein powder | 80 | 20 | olive oil | 100 | feed-deprived | after 3 hrs | 3.20 |
| Example 11 | oxidized Q10 | soymilk powder | 80 | 20 | olive oil | 100 | feed-deprived | after 3 hrs | 3.05 |
| Example 12 | oxidized Q10 | sesame powder | 20 | 80 | olive oil | 100 | feed-deprived | after 3 hrs | 2.67 |
| Example 13 | oxidized Q10 | sesame powder | 80 | 20 | olive oil | 100 | feed-deprived | after 3 hrs | 1.87 |
| Example 14 | oxidized Q10 | soy protein hydrolyzate | 90 | 10 | olive oil | 100 | feed-deprived | after 3 hrs | 2.62 |
| Example 15 | oxidized Q10 | soy protein powder | 95 | 5 | olive oil | 100 | feed-deprived | after 3 hrs | 2.45 |
| Example 16 | oxidized Q10 | toasted soy flour | 20 | 80 | olive oil | 100 | feed-deprived | after 3 hrs | 2.40 |
| Example 17 | oxidized Q10 | coffee bean powder | 20 | 80 | olive oil | 100 | feed-deprived | after 3 his | 2.38 |
| Example 18 | oxidized Q10 | coffee bean powder | 80 | 20 | olive oil | 100 | feed-deprived | after 3 hrs | 1.34 |
| Example 19 | oxidized Q10 | soy protein powder | 99 | 1 | olive oil | 100 | feed-deprived | after 3 hrs | 1.80 |
| Example 20 | oxidized Q10 | wheat flour | 20 | 80 | olive oil | 100 | feed-deprived | after 3 hrs | 1.77 |
| Comparative Example 1 | oxidized Q10 | — | 100 | 0 | olive oil | 100 | feed-deprived | after 3 hrs | 1.02 |
| Example 21 | reduced Q10 | toasted soy flour | 20 | 80 | water | 100 | feed-deprived | after 3 hrs | 4.40 |
| Comparative Example 2 | reduced Q10 | — | 100 | 0 | olive oil | 100 | feed-deprived | after 3 hrs | 2.30 |

4. The composition of claim 1, wherein the ratio of the product to the coenzyme Q10 is at least 0.01:1.

5. A functional food, comprising the composition of claim 1.

6. The composition of claim 1, wherein the soy protein hydrolyzate has a protein content of 40% or more.

7. The composition of claim 1, wherein the seed ground powder is obtained by grinding one or more parts selected from the seed coat and the seed germ.

8. The composition of claim 7, wherein the seeds that are ground to make the powder are roasted or defatted.

9. The composition of claim 1, wherein the powder obtained from a seed extract is obtained by drying an extract from one or more parts of the seed selected from the group consisting of the seed coat and the seed germ, wherein the seed coat or seed germ is extracted by squeezing or by treatment with water or an alcohol-containing aqueous solvent.

10. The composition of claim 1, wherein the seed ground powder and/or the powder obtained from a seed extract are obtained from at least one seed of the pea family (*Fabaceae*).

11. The composition of claim 1, wherein the seed ground powder and/or the powder obtained from a seed extract are obtained from at least one soy seed (*Glycine max*).

12. The composition of claim 11, wherein the powder obtained from the at least one soy seed is a whole soy powder or a toasted whole soy flour, or a defatted soy powder or a toasted defatted soy flour.

13. The composition of claim 11, wherein the powder obtained from at least one soy seed is a soymilk powder, a soy protein powder or a soy protein hydrolyzate powder.

* * * * *